(12) United States Patent
Platzek et al.

(10) Patent No.: US 6,495,118 B1
(45) Date of Patent: Dec. 17, 2002

(54) LIPOPHILIC METAL COMPLEXES FOR NECROSIS AND INFARCTION IMAGING

(75) Inventors: Johannes Platzek, Berlin (DE); Ulrich Speck, Berlin (DE); Ulrich Niedballa, Berlin (DE); Bernd Radüchel, Berlin (DE); Hanns Joachim Weinmann, Berlin (DE); Wolfgang Ebert, Mahlow (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/159,657

(22) Filed: Sep. 24, 1998

Related U.S. Application Data

(60) Provisional application No. 60/060,977, filed on Oct. 6, 1997.

(30) Foreign Application Priority Data

Sep. 26, 1997 (DE) .......................... 197 44 004

(51) Int. Cl.⁷ ........................ A61K 51/00; A61M 36/14
(52) U.S. Cl. .................. 424/9.1; 534/7; 534/10; 534/14; 424/1.11; 424/1.65
(58) Field of Search .................. 424/1.11, 1.65, 424/1.69, 9.3, 9.1, 9.4, 9.5, 9.6, 9.7, 9.8; 534/7, 10–16

(56) References Cited

U.S. PATENT DOCUMENTS

| | | |
|---|---|---|
| 4,480,008 A | 10/1984 | Farronato et al. |
| 4,916,246 A | 4/1990 | Felder et al. |
| 4,980,502 A | 12/1990 | Felder et al. |
| 5,132,409 A | 7/1992 | Felder et al. |
| 5,182,370 A | 1/1993 | Felder et al. |
| 5,250,285 A | 10/1993 | Lauffer et al. |
| 5,318,771 A | 6/1994 | Lauffer et al. |
| 5,358,704 A | 10/1994 | Desreux et al. |
| 5,422,096 A | 6/1995 | Lauffer et al. |
| 5,453,264 A | 9/1995 | Mori et al. |
| 5,457,183 A | 10/1995 | Sessler et al. |
| 5,527,522 A * | 6/1996 | Lauffer et al. ........... 424/9.362 |
| 5,575,986 A | 11/1996 | Mori et al. |
| 5,580,543 A | 12/1996 | Sessler et al. |
| 5,582,814 A | 12/1996 | Scott et al. |
| 5,583,220 A | 12/1996 | Sessler et al. |
| 5,587,371 A | 12/1996 | Sessler et al. |
| 5,599,923 A | 2/1997 | Sessler et al. |
| 5,622,946 A | 4/1997 | Sessler et al. |
| 5,628,982 A | 5/1997 | Lauffer et al. |
| 5,632,970 A | 5/1997 | Sessler et al. |
| 5,695,739 A | 12/1997 | Schmitt-Willich et al. |
| 5,798,092 A | 8/1998 | Schmitt-Willich et al. |
| 5,801,229 A | 9/1998 | Sessler et al. |
| 6,013,241 A * | 11/2000 | Marchal et al. ............ 424/1.65 |

FOREIGN PATENT DOCUMENTS

| | | |
|---|---|---|
| DE | 1960303 | 7/1997 |
| DE | 19603033 * | 7/1997 |
| EP | 0 230 893 | 6/1990 |
| EP | 0 405 704 | 12/1994 |
| EP | 0 325 762 | 3/1995 |
| EP | 0603403 | 10/1997 |
| WO | WO86/06605 | 11/1986 |
| WO | WO95/28179 | 10/1995 |
| WO | 95/31219 * | 11/1995 |
| WO | WO95/31219 | 11/1995 |
| WO | 9623526 * | 8/1996 |
| WO | WO96/23526 | 8/1996 |
| WO | WO97/30734 | 8/1997 |
| WO | 99/17809 | 4/1999 |

OTHER PUBLICATIONS

Patent Abstracts of Japan, vol. 011, No. 063, Feb. 26, 1987.
Patent Abstracts of Japan, vol. 9, No. 324, Dec. 19, 1985.

* cited by examiner

*Primary Examiner*—Dameron L. Jones
(74) *Attorney, Agent, or Firm*—Millen, White, Zelano & Branigan, P.C.

(57) ABSTRACT

This invention describes the use of metal complexes that have a plasma protein bond of at least 10% as imaging diagnostic agents for locating an infarction or a necrosis using lasting positive visualization.

14 Claims, 4 Drawing Sheets

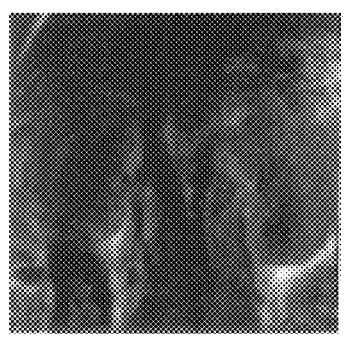  
precontrast | 15 min p.i. (300 μmol/kg) | 6 hours p.i. (300 μmol/kg)
FIG. 1a FIG. 1b FIG. 1c

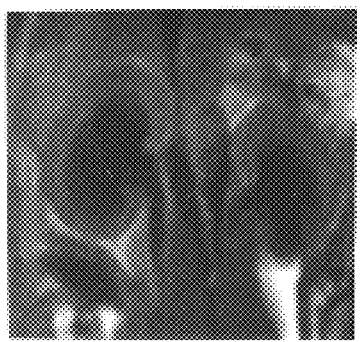  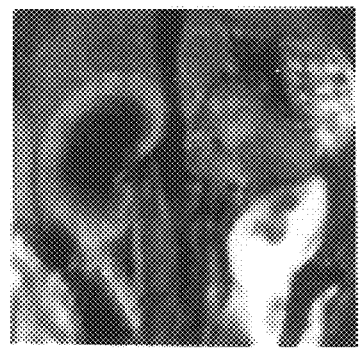
precontrast     5 min p.i. (500 μmol/kg)     5 hours p.i. (500 μmol/kg)
FIG. 2a     FIG. 2b     FIG. 2c

Infarction Imaging with MS-325 in Rats precontrast 6.5 minutes p.i.

60 minutes p.i.

19 hours p.i.

LIPOPHILIC METAL COMPLEXES FOR NECROSIS AND INFARCTION IMAGING

This application claims the benefit of the filing date of U.S. Provisional Application Serial No. 60/060,977 filed Oct. 6, 1997.

The invention relates to the subject that is characterized in the claims, i.e., the use of metal complexes that have a plasma protein bond of at least 10% as imaging diagnostic agents for locating an infarction or a necrosis based on the persistent accumulation of substances in the infarction or necrosis area.

Detection, location, and monitoring of necroses or infarctions is an important area in medicine. Myocardial infarction does not immediately result in irretrievable, non-functioning tissue; rather, it initiates a dynamic process that extends over a prolonged period (weeks to months). The disease proceeds in about three phases, which overlap rather than being distinctly separated from one another. The first phase, the development of myocardial infarction, comprises the 24 hours after the infarction, in which the destruction progresses like a shock wave (wave front phenomenon) from the subendocardium to the myocardium. The second phase, the already existing infarction, comprises the stabilization of the area in which the formation of fibers (fibrosis) takes place as a healing process. The third phase, the healed infarction, begins after all destroyed tissue is replaced by fibrous scar tissue. During this period, extensive restructuring takes place.

Up until now, no precise and reliable process has been known that would make it possible to diagnose the current phase of a myocardial infarction in a living patient. For evaluating a myocardial infarction, it is of decisive importance to know the extent of the portion of tissue that is definitively lost in the infarction and at what point the loss took place since the type of treatment depends on this information.

Infarctions occur not only in the myocardium but also in other tissues, especially in the brain.

While infarction can be healed to a certain extent, in the case of necrosis, locally limited tissue death, only the harmful sequelae for the rest of the organism can be prevented or at least mitigated. Necroses can develop in many ways: due to injuries, chemicals, oxygen deficits, or radiation. As with infarction, knowing the extent and nature of a necrosis is important for further medical treatment.

It is known that infarction and necrosis can be represented by antibodies that are directed against biomolecules that occur intracellularly and by porphyrins, metalloporphyrins and their derivatives. Antibodies and porphyrins can be produced only at great expense, however, and are problematical in terms of handling and compatibility in several respects.

It has now been shown that, surprisingly enough, metal complexes that have a plasm protein bond of at least 10% are suitable as imaging diagnostic agents for locating necroses that are produced by infarction or caused in some other way. In this case, the basic advantage consists of a persistent positive (bright) dyeing of necrotic areas with little to no signal enhancement of the environs. Non-protein-bonded, otherwise comparable complexes lead for only a short time to signal enhancement of well-perfused tissue, whereby underperfused—even vital—tissues remain unaffected. The blood supply to the tissues can also be detected using $T_2$ or $T_2$-star (susceptibility) effects, but differentiates non-vital from necrotic tissue. The plasma protein bond is, as is familiar to one skilled in the art, determined by equilibrium dialysis.

Preferably suitable are metal complexes that have a plasma protein bond of at least 50%, especially preferably of at least 80%. The metal complexes according to the invention have a molecular weight of at least 350 Da, and preferably at least 400 Da.

They have a $T^1$-relaxivity of at least 2.0 $[s^{-1}mM^{-1}]$, measured at 37° C. and 20 MHz in plasma (see, e.g., Chem. Rev. 1987, 87, 901). Their stability constant is at least $10^{15}$ (logK=15).

The metal complexes according to the invention are metal derivatives of, e.g., polyaminopolycarboxylic acids, polyaminopolyphosphonic acids, porphyrins, texaphyrins, sapphyrins, peptides and their derivatives, as they are described in, e.g.,

| | |
|---|---|
| U.S. Pat. No. 5,403,576 | WO 94/27644 |
| EP 452 392 | EP 391 766 |
| U.S. Pat. No. 5,512,294 | U.S. Pat. No. 5,536,491 |
| WO 95/09848 | U.S. Pat. No. 5,462,725 |
| WO 95/32741 | EP 425571 |
| U.S. Pat. No. 5,562,894 | WO 95/32004 |
| U.S. Pat. No. 5,407,657 | U.S. Pat. No. 5,370,860 |
| U.S. Pat. No. 5,463,030 | WO 94/10182 |
| JP 05186372 | U.S. Pat. No. 5,277,895 |
| WO 93/16375 | EP 413405 |
| DE 43 02 287 | EP 352218 |
| DE 40 11 684 | EP 405704 |
| DE 38 34 704 | EP 292689 |
| WO 97/26017 | EP 230893 |
| WO 95/28179 | U.S. Pat. No. 5,318,771 |
| WO 89/05802 | U.S. Pat. No. 5,422,096 |
| U.S. Pat. No. 4,899,755 | U.S. Pat. No. 5,527522 |
| U.S. Pat. No. 5,250,285 | WO 93/03351 |
| WO 91/03200 | WO 96/23526 |
| EP 0722739 | WP 95/28392 |
| EP 165716 | EP 540075 |
| U.S. Pat. No. 5,480,990 | WO 95/32192 |
| WO 95/31219 | U.S. Pat. No. 5,358,704 |
| U.S. Pat. No. 5,466,438 | WO 92/11232 |
| WO 95/31444 | WO 95/15319 |
| WO 95/09161 | U.S. Pat. No. 5,453,264 |
| JP 05186372 | EP 661279 |
| WO 94/03593 | WO 97/30734 |
| WO 97/30733 | DE 44 05 140 |
| GB 8903023 | U.S. Pat. No. 4,880,008. |
| U.S. Pat. No. 5,583,220 | |

If the metal complexes according to the invention are used for NMR diagnosis, the metal must be paramagnetic. This can be an element from the series of transition metals or lanthanides. Suitable ions include those of the elements iron, manganese, gadolinium, and dysprosium.

If the metal complexes according to the invention are used for radiodiagnosis, the metal must be radioactive. This can be an isotope from the series of elements Tc, In, Rh, Ga, Sc, Bi, Y, Fe, Sm, Ho, Co, Cu, Gd, and Eu.

As suitable chelating agents, the following can be mentioned by way of example:

2-(4-Ethoxybenzyl)-3,6,9-tris(carboxymethyl)-3,6,9-triazaundecane-1,11-dicarboxylic acid (ligand of Eovist®, EP 405704

2-(4-benzyloxybenzyl)-3,6,9-tris(carboxymethyl)-3,6,9-triazaundecane-1,11-dicarboxylic acid, EP 405704

2-(4-butylbenzyl)-3,6,9-tris(carboxymethyl)-3,6,9-triazaundecane-1,11-dicarboxylic acid, WO 95/28179

2,5,8,11-tetrakis(carboxymethyl)-2,5,8,11-tetraazabicyclo[10,4,0]-hexadecane, U.S. Pat. No. 5,358,704

2,5,12,15-tetrakis(carboxymethyl)-2,5,12,15-tetraazatricyclo[10,4,0,0$^{6,11}$]-icosane, U.S. Pat. No. 5,358,704

10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane, WO 97/26017

10-[2-hydroxy-4-aza-5-oxo-7-oxa-10,10,11,11,12,12,13,13,14,14,15,15,16,16,17,17,17,-heptadecafluoroheptadecyl]-1,4,7-tris(carboxymethyl)-1,4,7,10-tetraazacyclododecane, WO 97/26017

2-[1,4,7,10-tetraaza-4,7,10-tris(carboxymethyl) cyclododecan-1-yl]-3-benzyloxypropionic acid, WO 89/05802

2-benzyloxymethyl-3,6,9-tris(carboxymethyl)-3,6,9-triazaundecane-1,11-dicarboxylic acid, EP 230893

DTPA-Lys-Asp-Asp-4-pentylbicyclo[2,2,2]-octane-1-carboxylic acid, Mallinckrodt MP-2269, Vancouver SMRM, April 1997

4-[hydroxymethyl-(4,4-diphenyl)cyclohexyloxy-phosphoric acid diester]-3,6,9-carboxymethyl-3,6,9-triazaundecane-1,11-dicarboxylic acid (MS-325), WO 96/23526

4-[hydroxymethyl-(10-phenyl)-decyloxy-phosphoric acid diester]-3,6,9-carboxymethyl-3,6,9-triazaundecane-1,11-dicarboxylic acid (MS-323, WO 96/23526)

N-(4-Decylphenylcarbamoylmethyl)-diethylenetriamine-N,N',N'',N''-tetracetic acid, EP 603403

4,5-Diethyl-10,23-dimethyl-9,24-bis(3-hydroxypropyl)-16,17-bis[2-[2-(2-methoxyethoxy)ethoxy]-13,20,25,26,27-pentaazapentacyclo [20.2.1.]$^{3,6}$.18,11.0$^{14,19}$] heptacosa-3,5,8,10,12,14,16,18,20,22,24-undecane. U.S. Pat. No. 5,583,220.

The production of the pharmaceutical agents is carried out in a way known in the art by the corresponding complex compounds—optionally with the addition of the additives that are commonly used in galenicals—being suspended or dissolved in an aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca complexes that correspond to the metal complexes according to the invention) or—if necessary—electrolytes such as, for example, sodium chloride or—if necessary—antioxidants such as, for example, ascorbic acid.

If suspensions or solutions of the agents according to the invention in water or in a physiological salt solution are desired for enteral or parenteral administration or for other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substances for taste correction [for example, ethereal oils].

In principle, it is also possible to produce the pharmaceutical agents without isolating the complexes. Special care must always be taken to perform chelation in such a way that the complexes according to the invention are virtually free of uncomplexed metal ions that have a toxic action.

This can be ensured with the aid of, for example, color indicators such as xylenol orange by control titration during the production process. The invention therefore also relates to the process for the production of complex compounds and their salts. As a final precaution, there remains purification of the isolated complex.

The pharmaceutical agents preferably contain 0.1 $\mu$mol–1 mol/l of the complex and are generally dosed in amounts of 0.0001–5 mmol/kg. They are intended for enteral and parenteral administration. The complex compounds are used 1. for NMR diagnosis in the form of complexes of them with the ions of elements with atomic numbers 21–29, 42, 44 and 58–70;
2. for radiodiagnosis in the form of complexes of them with the radioisotopes of elements with atomic numbers 27, 29, 31, 32, 37–39, 43, 49, 62, 64, 70, 75 and 77.

The agents meet the varied requirements for suitability as contrast media for nuclear spin tomography. They are thus extremely well suited for improving the image, obtained with the aid of the nuclear spin tomograph, as regards its informational value after oral or parenteral administration by increasing the signal intensity. They also show the great effectiveness that is necessary to burden the body with the smallest possible amounts of foreign substances, and the good compatibility that is necessary to preserve the noninvasive nature of the studies.

The good water solubility and low osmolality of the agents make it possible to produce highly concentrated solutions, i.e., to keep the volume load on the circulation within reasonable bounds and to offset the dilution by bodily fluids. In addition, the agents have not only high stability in vitro, but also surprisingly high stability in vivo, so that release or exchange of the bonded ions—which are inherently toxic—in the complexes occurs only extremely slowly within the time during which the contrast media are completely eliminated.

In general, the agents for use as NMR diagnostic agents are dosed in amounts of 0.0001–5 mmol/kg, preferably 0.005–0.5 mmol/kg. Owing to their advantageous radioactive properties and the good stability of the complex compounds contained therein, the agents are also suitable as radiodiagnostic agents. Details on such use and dosage are described in, e.g., "Radiotracers for Medical Applications," CRC Press, Boca Raton, Fla.

In in-vivo administration of the agents, the latter can be administered together with a suitable vehicle such as, for example, serum or a physiological common salt solution or together with a protein such as, for example, human serum albumin. In this case, the dosage depends on the type of cellular disruption, the metal ion used, and the type of imaging method.

The agents are usually administered parenterally, preferably i.v. They can also be administered—as already discussed—intravascularly or interstitially/intracutaneously.

BRIEF DESCRIPTION OF THE DRAWINGS

FIGS. 1a–c are MRI images of a rat with induced renal infarctions

FIGS. 2a–c are MRI images of a rat with induced renal infarctions

FIG. 4a is precontrast

FIG. 4b is 6.5 minutes p.i.

FIG. 4c is 60 minutes p.i.

FIG. 4d is 19 hours p.i.

The examples below are used to give a more detailed explanation of the subject of the invention:

MRI Experiments on Animals with Induced Renal Infarctions

Enhancement in the MRI experiment was studied after one-time intravenous administration of the substance Eovist® in animals with experimentally induced renal necroses or infarctions. Plasma protein bond: 10% (Europ. Workshop on Magn. Reson. in Medicine, Santiago de Compostela, Spain, Sep. 28–30, 1994).

The induction of the renal infarctions was carried out on anesthetized (Rompun®/Ketavet®, i.p.) rats (Han. Wistar, Schering SPF, about 200 g of body weight) by occlusion of a (caudal) branch of the left renal artery. The contrast medium was administered (dose: 300 or 500 μmol of Gd/kg of body weight) about 24 hours after the induction of infarction. The animals were studied before and up to 24 hours after contrast medium administration by MR-tomography (SISCO SIS 85, 2 tesla; SE sequence, $T_R$: 400 ms, $T_E$: 15 ms, nt=4, ni=128, FOV: 12–7 cm, SD≈3 mm, 1 layer each axial or coronary).

After the MRI experiments were completed, the anesthetized animals were sacrificed by exsanguination (via the V. cava), and both kidneys were prepared. To verify the infarction (size and position), the left (infarcted) kidney was removed and sliced into disks, and then NBT ("vital") coloring was carried out.

Before the contrast medium was administered, no differentiation was possible between vital and avital (infarcted) areas in the (left, treated) kidney (see FIGS. 1a, 2a).

Immediately after substance administration, the nonperfused portion of the kidneys in each case was shown as a hypointense area (see FIGS. 1b, 2b). Starting at about 15–30 minutes p.i., the signal intensity increased somewhat in the non-perfused area or the size of the delimited (low-signal) area decreased (→slow diffusion in the necrosis). In the late phase (about 4–6 hours p.i.), a considerable signal increase (enhancement) in the necrotic area of the kidneys was noted in all of the animals studied (see FIGS. 1c, 2c). The delineation of the necrotic area in the MRI experiment correlated very well with the results of the histological "vital" coloring.

MRI Experiments on Animals with Induced Myocardial Infarctions

Figure 3A:
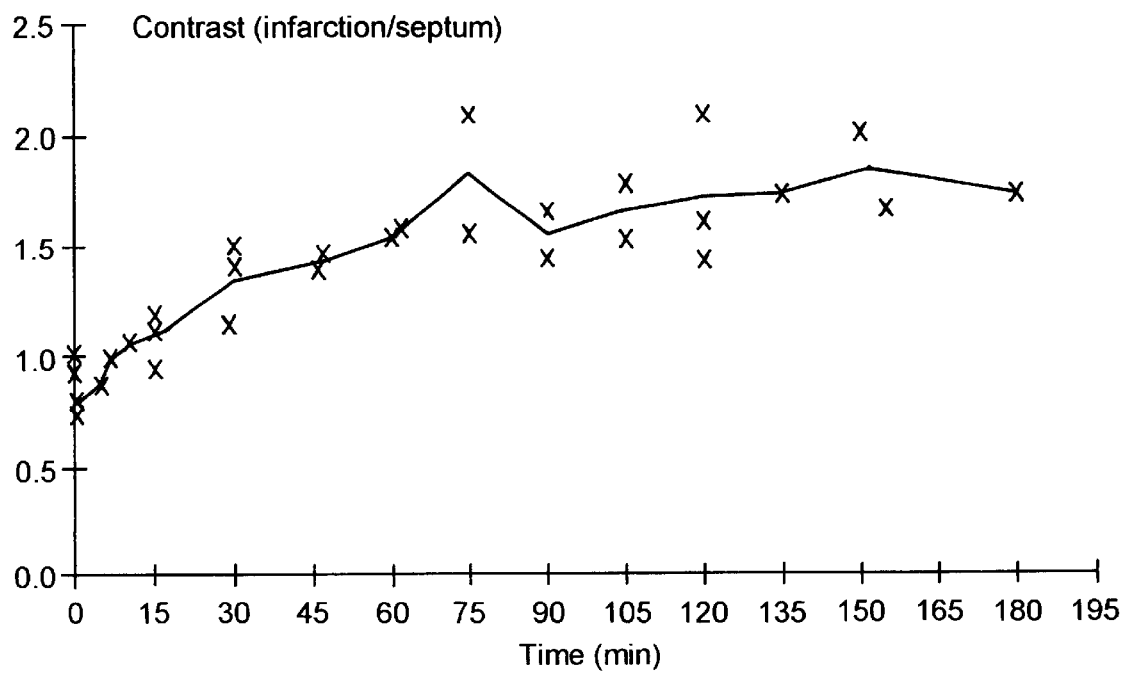
FIG. 3a is a graph of Contrast (infarction in Myocardium) vs time (0–180 minutes after i.v. administration of contrast medium)

Necroselective enhancement was studied after one-time intravenous administration of the substance MS-325 (WO 96/23526, Example 10, Gd-DTPA derivative) in animals with experimentally induced myocardial infarctions in the MRI experiment. The induction of the myocardial infarctions was carried out on anesthetized (Domitor®/Dormicum® i.m.) rats (Han. Wistar, Schering SPF, male, about 300 g of body weight, N=10) by occlusion of the left coronary artery. The contrast medium was administered (initial solution diluted with blood, dose 100 μmol/kg, i.v. bolus) 24 hours after the induction of infarction. The animals were studied before and up to 3 hours (1, 5, 10, 15, 30, 45, 60, 75, 90, 105, 120, 135, 150 and 180 minutes) p.i. (see FIG. 3a) continuously and 24 hours after the contrast medium administration by MR tomography (SE, SAT, EKG-triggered, $T_R$: about 400 ms, $T_E$: 10 ms, nt=4, Ma: 128*256, FOV: 7*7 cm, SD≈3 mm, 1 layer each axial) (see FIGS. 4a–d).

After the 24 hours p.i., the animals—in the MRT—were killed by a narcotic overdose, and an MRI experiment on "freshly-killed" animals (no artifacts of movement) was performed. To verify the infarction (size and position), the heart was prepared, cut into disks and subjected to coloring with NBT (nitro blue tetrazolinium chloride). Subjective evaluation of the enhancement and correlation with the colored tissue were carried out. The signal intensities were standardized to a GD-DTPA solution (0.25 mmol/l) and the percentage enhancement S1 post–S1 pre)/S1 pre 100% and the contrast S1 inf/S1 myocard were calculated.

In the healthy myocardium (septum) and in the muscle, maximum enhancement was shown immediately after the administration of substance with 100% or 60%. The signal intensity then dropped and reached a value of between 10 and 20% after 150 minutes (see FIG. 3b).

Figure 3B:
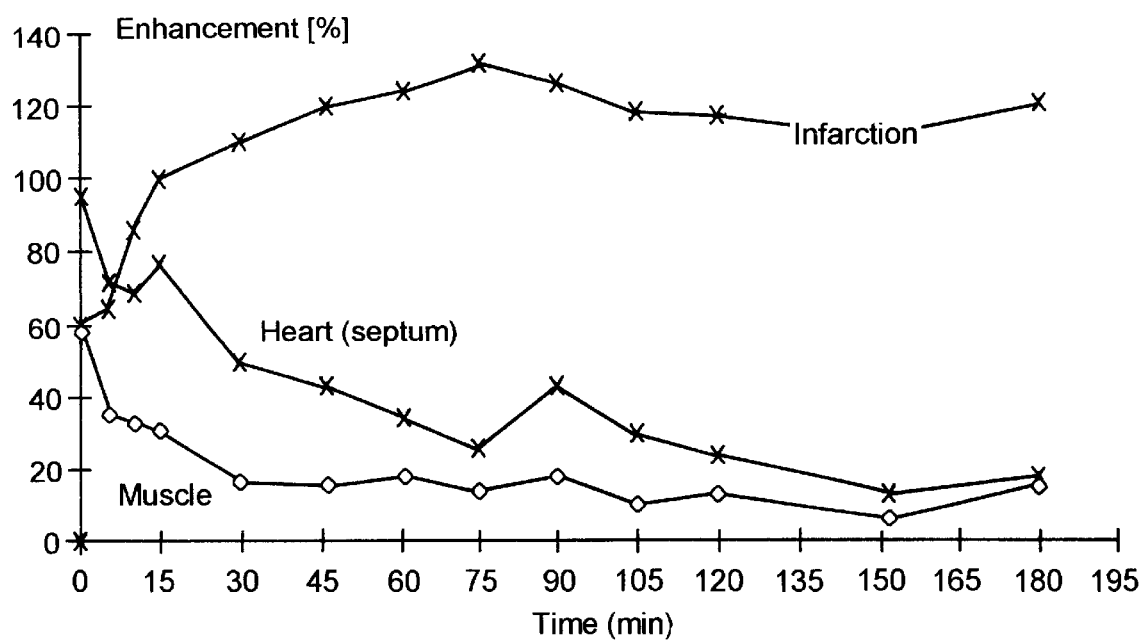
FIG. 3b is a graph of Percentage Enhancement vs time (0–180 minutes after i.v. administration of contrast medium)
Figure 4A:
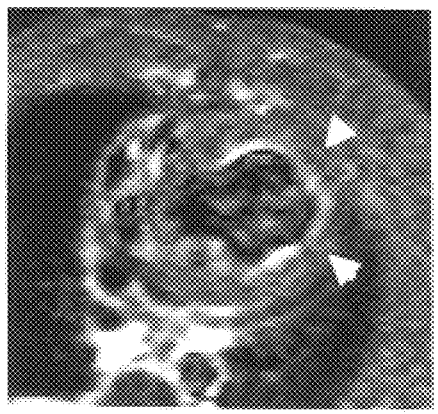
FIGS. 4a–d are four MRI images of a rat (Han. Wistar, Schering SPF, male, ≈300 g) with myocardial infarction that is induced—by occulsion of the left coronary artery—before and after administration of MS-325 (100 $\mu$mol of Gd/kg of body weight). (MR technology: SE_SAT, EKG-triggered, $T_R$: about 400 ms, $T_E$: 10 ms, nt=4, Ma: 128*256, FOV: 7*7 cm, SD≈3 mm, 1 layer, axial)
Figure 4B:
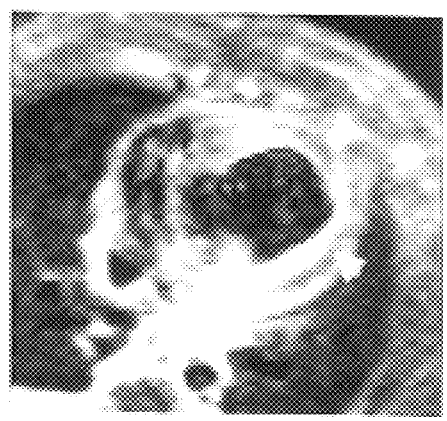
Figure 4C:
Figure 4D:
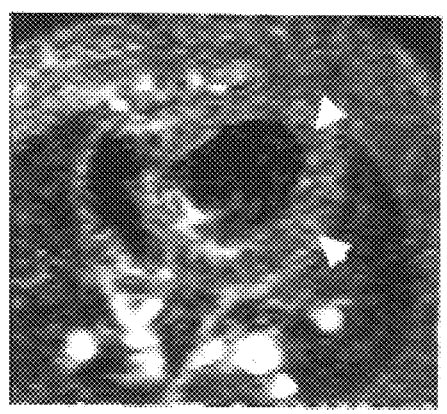

In the infarcted area, however, the signal intensity increased within 60–75 minutes to about 130% and then remained almost unchanged (up to 180 minutes) (see FIG. 3b).

In contrast, it was possible to observe a negative contrast (S1 inf/S1 myocard<1) within the first 10 to 15 minutes. Starting approximately from the 30th minute, it was possible to ascertain a positive contrast (S1 inf/S1 myocard>1) (see FIG. 3b).

After one day p.i., approximately the starting intensity (≈5–15%) was again reached in all tissues, and a contrasting of the myocardial infarction (S1 inf/S1 myocard≈0.98) could no longer be detected.

MS-325 shows suitability as an infarction contrast medium.

What is claimed is:

1. A method of locating a necrosis in a patient comprising administering a metal complex having at least 10% bonding affinity to plasma protein and imaging areas of possible necrosis at a time after said administration sufficient for the positive enhancement of the image of said necrosis with respect to the environs thereof, wherein said metal complex is not a porphyrin.

2. A method according to claim 1, wherein said complex has a protein bonding affinity of at least 50%.

3. A method according to claim 1, wherein said complex has a protein bonding affinity of at least 80%.

4. A method according to claim 1, wherein said complex has a molecular weight that is greater than 350 Da.

5. A method according to claim 1, wherein said complex has a stability constant of at least $10^{15}$ (logK=15).

6. A method according to claim 1, wherein said complex contains a paramagnetic metal effective for NMR imaging.

7. A method according to claim 1, wherein said complex contains a radioactive metal for radiodiagnostic imaging.

8. A method according to claim 6, wherein said complex contains, as a paramagnetic metal, iron, manganese, gadolinium, or dysprosium.

9. A method according to claim 7, wherein said complex contains, as a radioactive metal isotope, Tc-99m, In, Rh, Ga, Sc, Bi, Y, Fe, Sm, Ho, Co, Cu, Gd, or Eu.

10. A method of claim 1 wherein said image is taken at least about one hour after said administration.

11. A method according to claim 1, wherein said complex has a relaxivity that is greater than 2.0 at 20 MHz and 37° C. in plasma.

12. A method of claim 1 wherein the ligand of said complex is 2-(4-Ethoxybenzyl)-3,6,9-tris(carboxymethyl)-3,6,9-triazaundecane-1,11-dicarboxylic acid, 2-(4-benzyloxybenzyl)-3,6,9-tris(carboxymethyl)-3,6,9-triazaundecane-1,11-dicarboxylic acid, 2-(4-butylbenzyl)-3,6,9-tris(carboxymethyl)-3,6,9-triazaundecane-1,11-dicarboxylicacid, 2,5,8,11-tetrakis(carboxymethyl)-2,5,8,11-tetraazabicyclo[10,4,0]-hexadecane, 2,5,12,15-tetrakis(carboxymethyl)-2,5,12,15-tetraazatricyclo [10,4,0,0$^{6,11}$]-icosane, 10-[1-methyl-2-oxo-3-aza-5-oxo-5-{4-perfluorooctylsulfonyl-piperazin-1-yl}-pentyl]1,4,7-tris(carboxymethyl)-1,4,7,1 0-tetraazacyclododecane, 10-[2-hydroxy-4-aza-5-oxo-7-oxa-10,10,11,11,12,12,13,13,14,14,15,15,16,16,17,17,17,-heptadecafluoroheptadecyl]-1,4,7-tris(carboxymethyl)-1,4,7,10-tetraazacyclododecane, 2-[1,4,7,10-tetraaza-4,7,10-tris(carboxymethyl)-cyclododecan-1-yl]-3-benzyloxypropionic acid, 2-benzyloxymethyl-3,6,9-tris(carboxymethyl)-3,6,9-triazaundecane-1,11-dicarboxylic acid, DTPA-Lys-Asp-Asp-4-pentylbicyclo[2,2,2]-octane-1-carboxylic acid, 4-[hydroxymethyl-(4,4-diphenyl)cyclohexyloxy-phosphoric acid diester]-3,6,9-carboxymethyl-3,6,9-triazaundecane-1,11-dicarboxylic acid, 4-[hydroxymethyl-(10-phenyl)-decyloxy-phosphoric acid diester]-3,6,9-carboxymethyl-3,6,9-triazaundecane-1,11-dicarboxylic acid, N-(4-decylphenylcarbamoylmethyl)-diethylenetriamine-N,N',N'',N''-tetraacetic acid, or 4,5-diethyl-10,23-dimethyl-9,24-bis(3-hydroxypropyl)-16,17-bis[2-[2-(2-methoxyethoxy]ethoxy]-13,20,25,26,27-pentaazapentacyclo[20.2.1]$^{3,6}$18,11.0$^{14,19}$] heptacosa-3,5,8,10,12,14,16,18,20,22,24-undecaene.

13. A method of claim 1 wherein said necrosis is an infarction.

14. A method of claim 1 wherein said time after administration is around 24 hours.

\* \* \* \* \*